United States Patent
Pang et al.

(10) Patent No.: US 11,774,589 B2
(45) Date of Patent: *Oct. 3, 2023

(54) DUAL FREQUENCY ULTRASOUND TRANSDUCER

(71) Applicant: FUJIFILM SONOSITE, INC., Bothell, WA (US)

(72) Inventors: Guofeng Pang, Ajax (CA); Oleg Ivanytskyy, Toronto (CA); Hossein Amini, Toronto (CA); Robert Kolaja, Toronto (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 59 days.

This patent is subject to a terminal disclaimer.

(21) Appl. No.: 17/522,293

(22) Filed: Nov. 9, 2021

(65) Prior Publication Data
US 2022/0066027 A1    Mar. 3, 2022

Related U.S. Application Data

(63) Continuation of application No. 16/051,060, filed on Jul. 31, 2018, now Pat. No. 11,169,265.
(Continued)

(51) Int. Cl.
*G01S 15/89*    (2006.01)

(52) U.S. Cl.
CPC ...... *G01S 15/8952* (2013.01); *G01S 15/8915* (2013.01); *G01S 15/8956* (2013.01); *G01S 15/8979* (2013.01)

(58) Field of Classification Search
CPC ............ G01S 15/8952; G01S 15/8956; G01S 15/8979; G01S 15/8915; G01S 7/52038;
(Continued)

(56) References Cited

U.S. PATENT DOCUMENTS 8,316,518 B2    11/2012    Lukacs et al.
8,674,524 B1    3/2014    Woerz et al.
(Continued)

FOREIGN PATENT DOCUMENTS

JP    2004363746    12/2004
JP    2010087965    4/2010
(Continued)

OTHER PUBLICATIONS

Extended European Search Report dated Dec. 17, 2021 in Application No. EP19796200.
(Continued)

*Primary Examiner* — Daniel L Murphy
(74) *Attorney, Agent, or Firm* — Colby Nipper PLLC

(57) ABSTRACT

A dual frequency ultrasound transducer includes a high frequency (HF) transducer and a low frequency (LF) transducer that is positioned behind the high frequency transducer. An intermediate layer is positioned between the low frequency transducer and the high frequency transducer to absorb high frequency ultrasound signals. An alignment feature on the low frequency transducer is positioned with respect to a fiducial that is marked at a known position with respect to high frequency transducer elements of the HF transducer to align low frequency transducer elements of the LF transducer with the HF transducer elements.

20 Claims, 9 Drawing Sheets

Related U.S. Application Data

(60) Provisional application No. 62/666,519, filed on May 3, 2018.

(58) Field of Classification Search
CPC ... G01S 7/52079; A61B 8/4494; A61B 8/481; B06B 2201/76; B06B 1/0622
USPC .......................................................... 367/7
See application file for complete search history.

(56) References Cited

U.S. PATENT DOCUMENTS

| | | | |
|---|---|---|---|
| 9,935,254 | B2 | 4/2018 | Lukacs et al. |
| 11,169,265 | B2 * | 11/2021 | Pang ................. B06B 1/0622 |
| 2008/0200813 | A1 | 8/2008 | Quistgaard |
| 2013/0207519 | A1 | 8/2013 | Chaggares et al. |
| 2017/0144192 | A1 | 5/2017 | Chaggares et al. |
| 2017/0282215 | A1 | 10/2017 | Chaggares et al. |

FOREIGN PATENT DOCUMENTS

| | | |
|---|---|---|
| JP | 2010233224 | 10/2010 |
| JP | 2012503370 | 2/2012 |
| WO | WO 2010/146136 A1 | 12/2010 |
| WO | 2017091632 | 6/2017 |

OTHER PUBLICATIONS

U.S. Appl. No. 16/051,060 (U.S. Pat. No. 11,169,265), filed Jul. 31, 2018 (Nov. 9, 2021).
Chaggares et al., U.S. Appl. No. 15/993,156, "High Frequency Ultrasound Transducer," filed May 30, 2018, 30 pages.
International Search Report dated Sep. 9, 2019 in International Application No. PCT/US2019/028832.
U.S. Appl. No. 16/051,060, filed Sep. 27, 2021 Issue Fee Payment.
U.S. Appl. No. 16/051,060, filed Jun. 28, 2021 Notice of Allowance.
U.S. Appl. No. 16/051,060, filed Jun. 17, 2021 Response after Ex Parte Quayle Action.
U.S. Appl. No. 16/051,060, filed Apr. 28, 2021 Ex Parte Quayle Action.
U.S. Appl. No. 16/051,060, filed Apr. 19, 2021 Response after Non-Final Office Action.
U.S. Appl. No. 16/051,060, filed Jan. 19, 2021 Non-Final Office Action.
"Foreign Office Action", JP Application No. 2020-561888, dated Mar. 28, 2023, 5 pages.

* cited by examiner

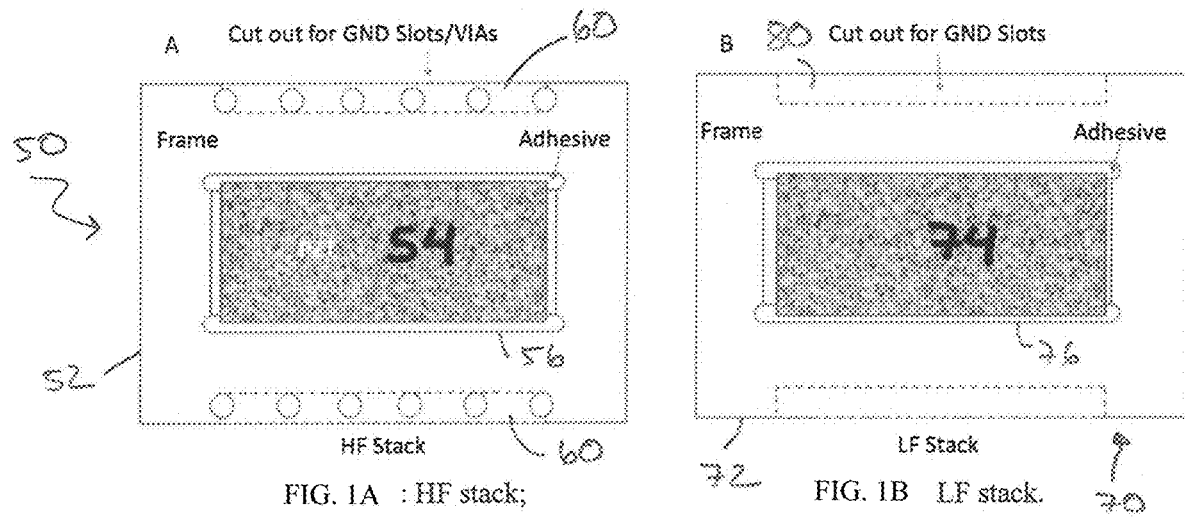
FIG. 1A : HF stack;  FIG. 1B  LF stack.
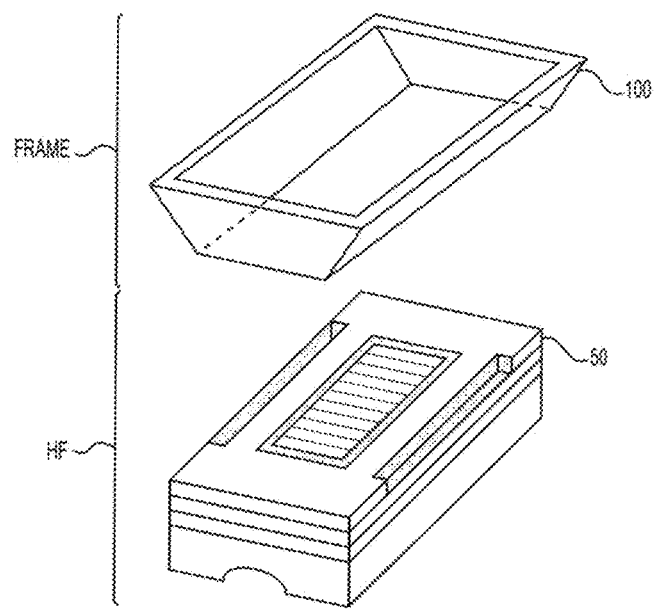
FIG. 2

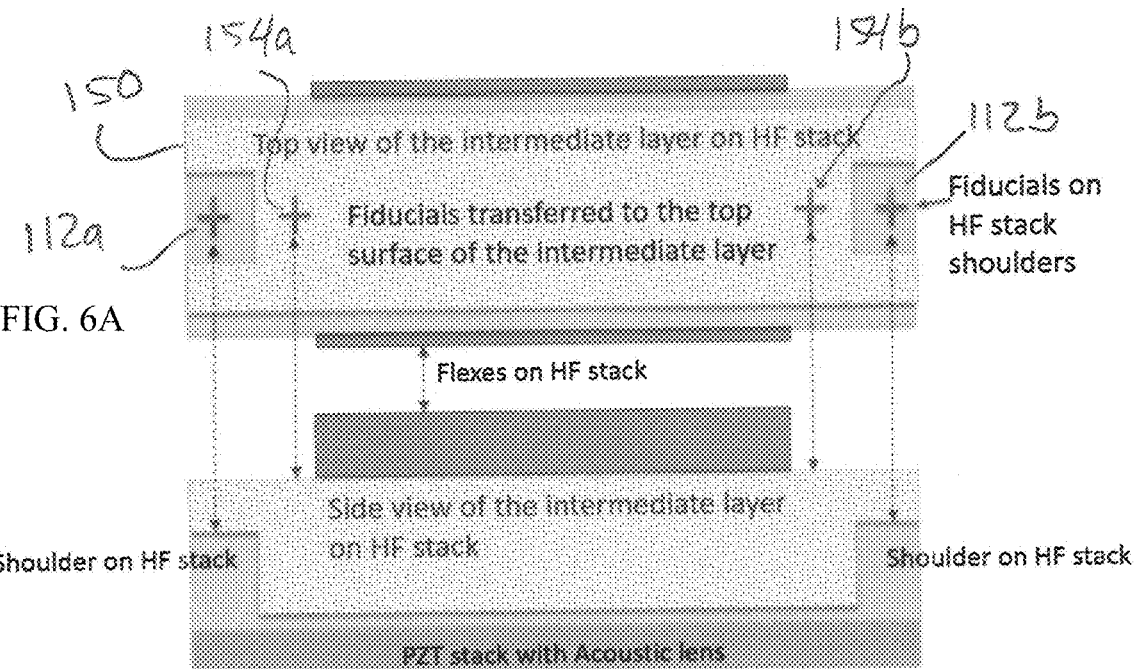
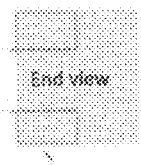
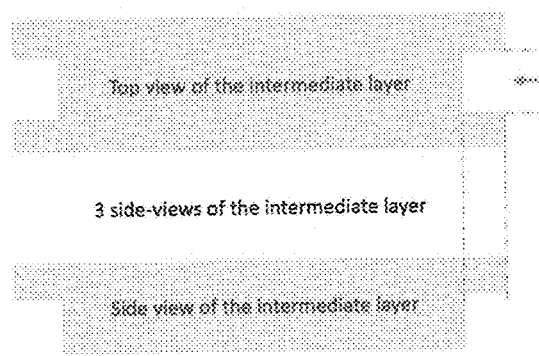
FIG. 6A
FIG. 6B
FIG. 6C
FIG. 6D
Figure 6A: The top/side view of the intermediate layer glued on a HF stack with alignment fiducials, Figures 6B-6D three side-views of the intermediate layer.

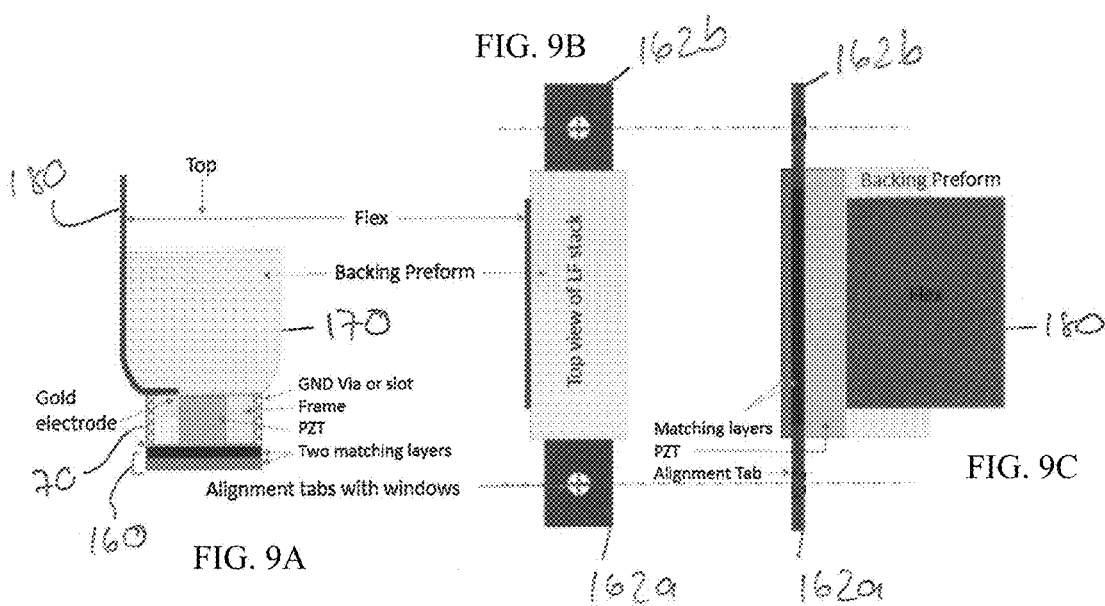
Figure 9A The cross-sectional view from backing down to PZT and matching layers: Figures 9B, 9C (Right and middle) LF stack with alignment features.

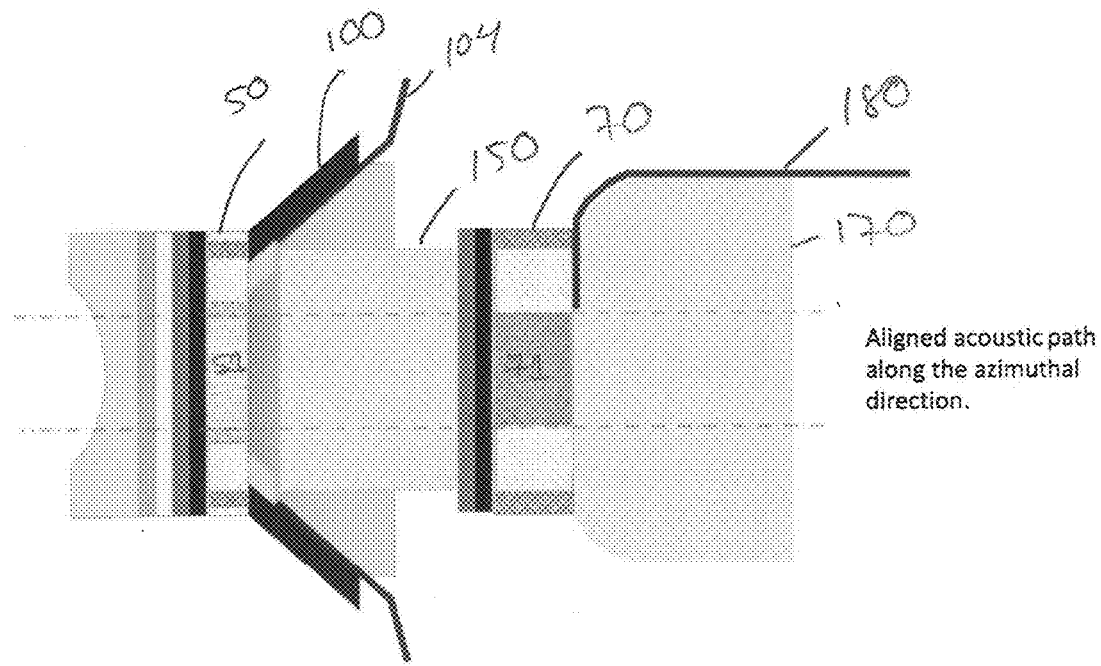
Figure 11: Cross-sectional view of an assembled dual frequency array.
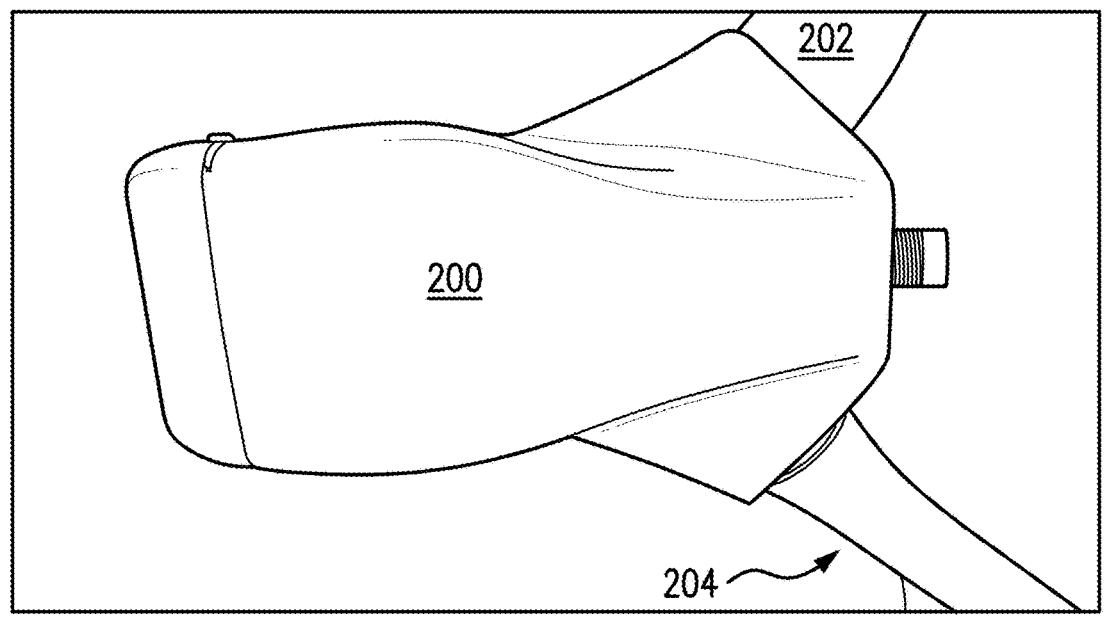
Figure 12: Completed assembly in a housing

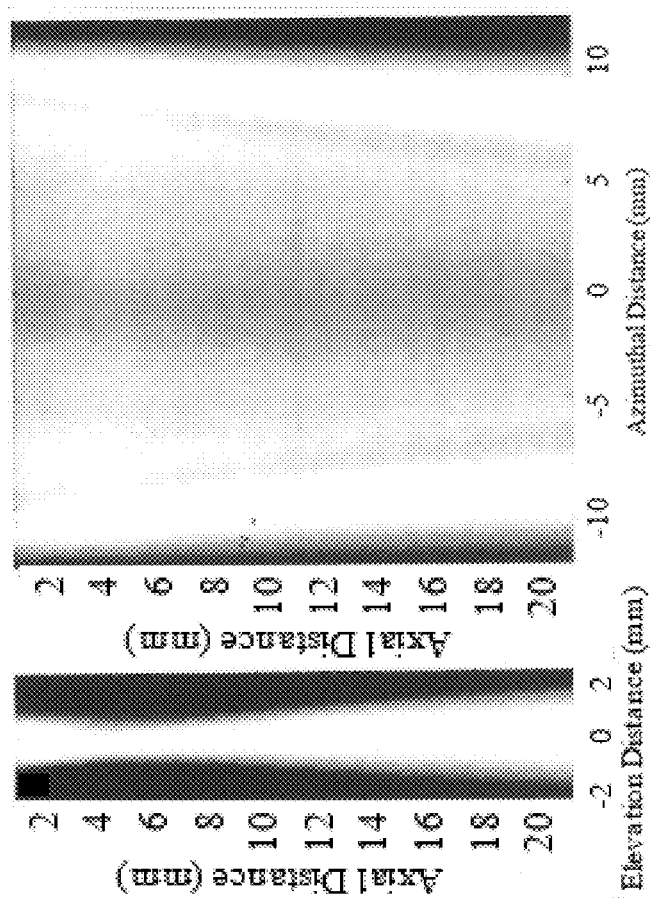
Figures 13A-13H Beam Plots from Low Frequency Transducer

DUAL FREQUENCY ULTRASOUND TRANSDUCER

CROSS-REFERENCE TO RELATED APPLICATION(S)

The present application is a continuation of U.S. patent application Ser. No. 16/051,060 filed Jul. 31, 2018, now allowed, which is related to, and claims the benefit of, U.S. Provisional Patent Application No. 62/666,519 filed May 3, 2018, which is herein incorporated by reference in its entirety.

STATEMENT REGARDING FEDERALLY SPONSORED RESEARCH

The subject of the preset application was made with government support under grant number 5100220, awarded by the National Institutes of Health (NIH)—Federal Reporting and Grant Number RO1CA189479. The Government has certain rights in the invention.

TECHNICAL FIELD

The disclosed technology relates to ultrasound transducers and in particular to dual frequency ultrasound transducers.

BACKGROUND

In conventional ultrasound imaging, ultrasonic acoustic signals are directed towards a region of interest and the corresponding reflected echo signals are detected. Characteristics of the echo signals such as their amplitude, phase shift, Doppler shift, power etc. are analyzed and quantified into pixel data that are used to create an image of or representation of flow. With conventional single transducer ultrasound imaging, the received ultrasound echo signals are in the same frequency range as the transmitted ultrasound signals.

Another approach to performing ultrasound imaging is to apply ultrasonic acoustic signals to the region of interest at one frequency and to capture and analyze the received echo signals at another frequency such as at one or more harmonics of the transmitted ultrasound signals. Typically, the harmonics have a frequency that is 3-5 times that of the transmitted signals. One specific use of harmonic imaging is imaging tissue with contrast agents. Contrast agents are generally fluid or lipid encapsulated microbubbles that are sized to resonate at a particular transmitted ultrasound frequency. Exposure to ultrasound in the body at the resonant frequency of the microbubbles, causes the bubbles to rupture and produce non-linear ultrasound echoes having a much higher frequency than the applied ultrasound. For example, non-linear microbubbles can be designed to resonate at 1-6 MHz but produce echo signals in the range of 10-30 MHz. The high frequency echo signals allow detailed images of tissue structures to be produced and studied such as the micro-vasculature surrounding tumors in clinical or pre-clinical settings.

The most conventional way of performing dual frequency imaging is with a mechanically scanned, single element transducer having confocal low and high frequency transducer elements. While such transducers work well, faster scanning can be performed with transducer arrays that can be electronically steered. Such transducers generally have a low frequency transducer array and a high frequency transducer array that are aligned with each other. One problem with dual frequency transducers is aligning the low and high frequency arrays. In a 30 MHz high frequency phased array, the element size (e.g. ½λ or less) is about 25 microns. At 50 MHz, the element size is approximately 15 microns. For comparison, a typical human hair is approximately 80 microns in diameter. The procedure required to align the arrays often requires making micro-adjustments to the position of the high and low frequency transducers on a wet bench and then adhering them together when the best match is found. This is both time consuming and costly. The technology discussed herein relates to an improved dual frequency transducer that is easier and/or less costly to manufacture.

SUMMARY

A dual frequency ultrasound transducer includes a high frequency transducer and a low frequency transducer that is positioned behind the high frequency transducer. An alignment feature on the low frequency transducer is positioned with respect to a fiducial that is marked at a known positioned with respect to the high frequency transducer. In one embodiment, one or more fiducials are marked on an intermediate layer that is positioned between the high frequency transducer and the low frequency transducer. The intermediate layer is configured to absorb high frequency ultrasound signals while passing lower frequency ultrasound signals.

In one embodiment, the high frequency transducer includes a support frame that includes an alignment post that fits with a cooperating slot or keyway on the intermediate layer to align the intermediate layer with the support frame and the high frequency transducer elements. One or more fiducials on the intermediate layer are positioned at locations referenced to the high frequency transducer elements to align the low frequency transducer to the high frequency transducer elements.

BRIEF DESCRIPTION OF THE DRAWINGS

FIG. 1A is a top view of a piezoelectric layer of a high frequency (HF) transducer in accordance with some embodiments of the disclosed technology;

FIG. 1B is a top view of a piezoelectric layer of a low frequency (LF) transducer in accordance with some embodiments of the disclosed technology;

FIG. 2 is a partial isometric view of a conductive frame and piezoelectric layer of a high frequency transducer array in accordance with some embodiments of the disclosed technology;

FIGS. 6A-6D are top, side and end views of an intermediate layer aligned with a high frequency transducer in accordance with an embodiment of the disclosed technology;

FIGS. 9A-9C are end, top and side views of a low frequency transducer in accordance with some embodiments of the disclosed technology;

FIG. 11 is a cross-sectional view of a dual frequency transducer showing an alignment of high and low frequency transducer elements in accordance with some embodiments of the disclosed technology;

FIG. 12 shows a housing for a dual frequency transducer in accordance with an embodiment of the disclosed technology; and FIGS. 13A-13H show a number of beam plots from a low frequency transducer in accordance with an embodiment of the disclosed technology.

DETAILED DESCRIPTION

Figure 3:
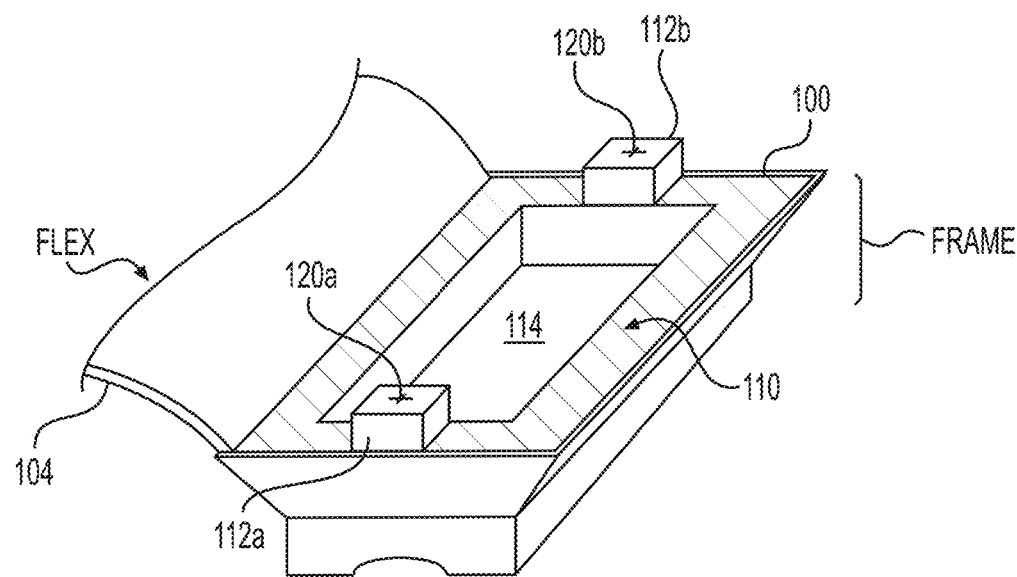
FIG. 3 is an isometric view of a piezoelectric layer, a flex circuit and a conductive frame with alignment features formed on a rear side of the frame in accordance with some embodiments of the disclosed technology.

The technology shown in the figures and described below relates to a dual frequency ultrasound transducer. Components of a dual frequency transducer are shown for the purpose of explaining how to make and use the disclosed technology. It will be appreciated that the illustrations are not necessarily drawn to scale.

FIG. 1 is a top view of a piezoelectric layer 50 for a high frequency ultrasound transducer in accordance with one embodiment of the disclosed technology. In one embodiment, the layer 50 has an outer frame 52 that surrounds a sheet 54 of PZT, single crystal piezoelectric or other known piezoelectric material. In one embodiment, the frame 52 is a pre-machined, non-conductive alumina ceramic with a center cut out area that is slightly larger than the outer dimensions of the sheet 54 of piezoelectric material. In other embodiments, the frame 52 can be made of a conductive material such as molybdenum or graphite. The frame 52 preferably has a coefficient of thermal expansion that is similar to that of the piezoelectric material so that the piezoelectric material doesn't crack during manufacture, handling or use. An adhesive 56 such as EPO-TEK 301 epoxy fills a gap between the frame and the piezoelectric material. The piezoelectric material 54 is diced with a patterning laser or a dicing saw to create a number (e.g. 128, 256 or fewer or a larger number) of piezoelectric elements (not separately shown). By surrounding the sheet 54 of piezoelectric material with the frame 52, the kerf cuts that define the individual transducer elements can extend across the entire width of the sheet of piezoelectric material.

If the frame 52 is made of a non-conductive material, a cut-out area or notch 60 on one or both sides of the frame is filled with a conductive epoxy or can include a number of conductive vias to provide an electrical path from a front surface of the frame to a rear surface of the frame. More details about the construction of an ultrasound transducer with a surrounding frame can be found in commonly-owned U.S. patent application Ser. No. 15/993,156 filed May 30, 2018 and U.S. Provisional Application No. 62/612,169 filed Dec. 29, 2017, which are herein incorporated by reference in their entireties.

FIG. 1B shows a piezoelectric layer 70 of a low frequency ultrasound transducer that in one embodiment, is constructed in the same manner as the piezoelectric layer of the high frequency transducer shown in FIG. 1A. An alumina frame 72 surrounds a sheet 74 of piezoelectric material. The frame 72 has a central opening that is sized to form a gap between the edges of the opening and the edges of the piezoelectric sheet 74. The gap is filled with a non-conductive epoxy 76. The low frequency array has fewer transducer elements than the high frequency transducer. In one embodiment, the low frequency transducer has 32 individually addressable transducer elements but could have fewer or more elements. A pair of cut-out areas or notches 80 on either side of the frame 72 can be filled with a conductive epoxy or can include conductive vias through the frame to provide an electrical path from a front surface of the low frequency array to the rear surface of the frame.

FIG. 2 is an isometric view of a conductive support frame 100 that is to be secured to a rear surface of the piezoelectric layer 50 of the high frequency transducer. The frame 100 supports one or more flex circuits (not shown) having signal traces therein that are electrically connected to corresponding electrodes on each of the high frequency transducer elements. In addition, the support frame 100 provides electromagnetic shielding for the rear surface of the transducer elements. A common ground electrode on the front surface of the piezoelectric layer 50 is connected to a ground plane in the flex circuits via a conductive path that includes the conductive support frame 100. In one embodiment, the support frame 100 is secured to the piezoelectric layer 50 with a conductive epoxy. Also shown in FIG. 2 are one or more matching layers and a lens that are positioned ahead of (e.g. in front of) the piezoelectric layer 50.

FIG. 3 shows one flex circuit 104 attached to the support frame 100. In some embodiments, the high frequency transducer includes two flex circuits with the signal traces of one flex circuit electrically coupled to the even numbered transducer elements and the signal traces of the other flex circuit electrically connected to the odd numbered transducer elements. Electrical connections are made from the individual transducer elements on the rear surface of the piezoelectric layer to the metal signal traces in the flex circuits. Connections between the transducer elements and the metal signal traces in the flex circuits can be made using the techniques described in U.S. Patent Publication No. 2017/0144192 or U.S. Pat. No. 8,316,518, which are herein incorporated by reference in their entireties. After the connections are made, an open back side of the support frame is filled with an epoxy material 110 such as EPO-TEK 301. In one embodiment, the height of the epoxy 110 in the frame extends above the rim of the support frame 100. As shown in FIG. 3, the epoxy 110 is molded or laser machined to form a pair of alignment posts 112a, 112b and a recess area 114 that is behind the high frequency transducer elements. In one embodiment, the depth of the recess area 114 is about 4.2 mm. The alignment posts 112a, 112b are configured to align an intermediate layer over the high frequency transducer as will be described below. A pair of fiducials 120a, 120b are marked with a laser on each alignment post at a known distance from the high frequency transducer elements. The fiducials 120a, 120b serve as a reference so that other components of the dual frequency transducer can be placed at known positions with respect to the high frequency transducer elements.

Figure 4:
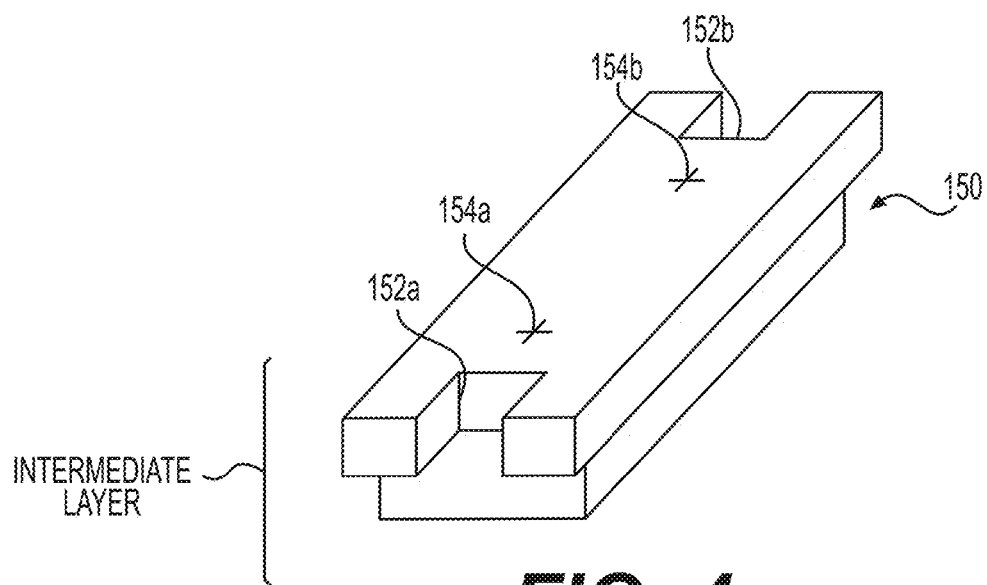
FIG. 4 is an isometric view of an intermediate layer to be positioned between the low frequency transducer and the high frequency transducer in accordance with some embodiments of the disclosed technology.

FIG. 4 illustrates one embodiment of an intermediate layer 150 that is placed behind the high frequency transducer. In one embodiment, the intermediate layer 150 is made of silicone powder-doped EPO-TEK 301 epoxy. The size of the silicone powder is in the nanometer range such that it highly attenuates high frequency (HF) ultrasound and passes low frequency (LF) ultrasound. The intermediate layer is sized to absorb high frequency ultrasound to a specified level, such as 65 dB, but to pass low frequency signals transmitted from, or to be received by, the low frequency transducer. The top of the intermediate layer 150 includes a pair of slots or keyways 152a, 152b that cooperate with the alignment posts 112a, 112b on the back side of the frame 100 to align the intermediate layer 150 at a known position with respect to transducer elements of the high frequency transducer. In one embodiment, the intermediate layer 150 is secured to the frame 100 using the same epoxy that fills the back side of the frame to avoid acoustic discontinuities at the bond line.

Once the intermediate layer is secured to the frame 100, additional fiducials 154a, 154b can be placed on the intermediate layer as measured from the fiducials 120a, 120b that are marked on the support frame (i.e. on the filler epoxy at the back side of the support frame).

Figure 5:
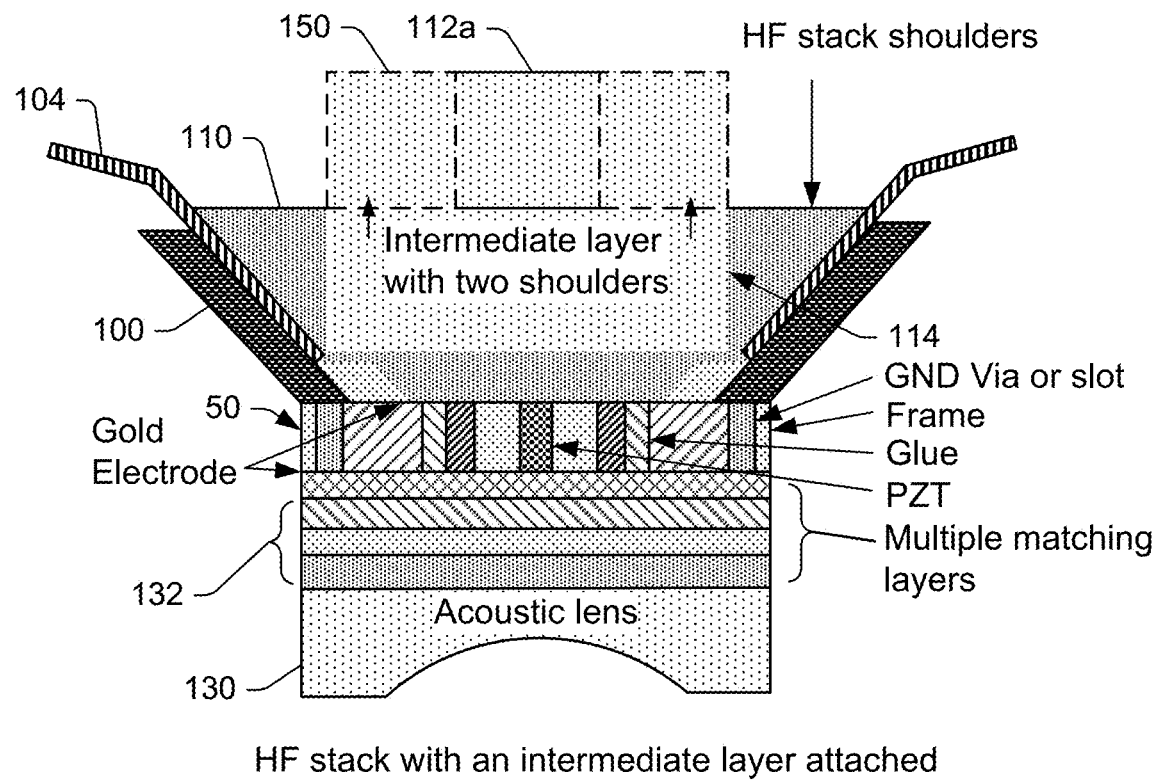
FIG. 5 is a cross-sectional view of a dual frequency transducer with the intermediate layer in place over a high frequency transducer.

FIG. 5 shows a cross section of the high frequency transducer with the intermediate layer 150 secured to the back of the support frame 100. As shown, the high frequency transducer comprises a lens 130 designed to focus the high frequency ultrasound signals at a specific depth. Typical lens materials include polymethylpentene (tradename TPX), cross-linked polystyrene (tradename Rexolite) or polybenzimidazone (tradename Celezole). However, other non-attenuating plastic materials could also be used. Behind the lens are one or more quarter wave matching layers 132 that match the impedance of the piezoelectric layer 50 to the impedance of the lens 130. The one or more matching layers are generally formed by adding particles to an epoxy to adjust its acoustic impedance. A metallic (e.g. gold or gold+chromium) common ground electrode is deposited on the front surface of the piezoelectric layer 50 and is electrically coupled to the conductive support frame 100 through the slots or vias in the frame 52 surrounding the PZT material. An applied metal coating on the rear or proximal surface of the piezoelectric layer is formed into conductive paths from individual transducer elements to the signal traces in the flex circuit. The layer of epoxy 110 covers the proximal side of the transducer elements and fills in the rear side of the support frame. In one embodiment, the recess 114 formed in the epoxy behind the high frequency transducer array is sized such that the intermediate layer is larger in the elevation and azimuthal dimensions of the transducer than the size of the transducer elements so that the intermediate layer extends over the ends of high frequency transducer elements.

FIGS. 6A-6D illustrate a pair fiducials 154a, 154b that are marked on a top surface of the intermediate layer 150. The fiducials 154a, 154b are measured with respect to the fiducials 112a, 112b that are marked on the epoxy in the support frame. The fiducials 154a, 154b are marked on the intermediate layer once the intermediate layer is secured to the support frame behind the high frequency transducer. In the embodiment shown, the fiducials 112a, 112b, 154a, 154b are crosses made with a laser.

Figure 7A:
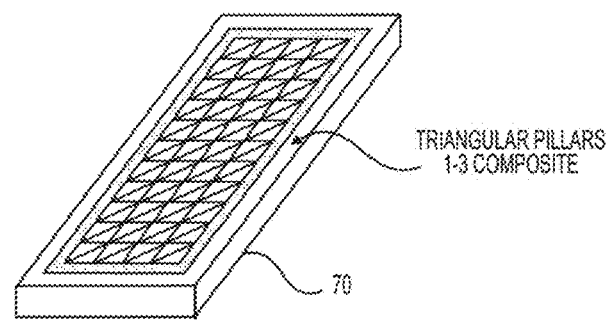
FIG. 7A is an isometric view of piezoelectric layer of a low frequency transducer in accordance with some embodiments of the disclosed technology.

FIG. 7A shows an embodiment of a piezoelectric layer 70 for the low frequency transducer. In the embodiment shown, the piezoelectric layer 70 also includes an alumina frame surrounding a sheet of PZT or other piezoelectric material.

Figure 7B:
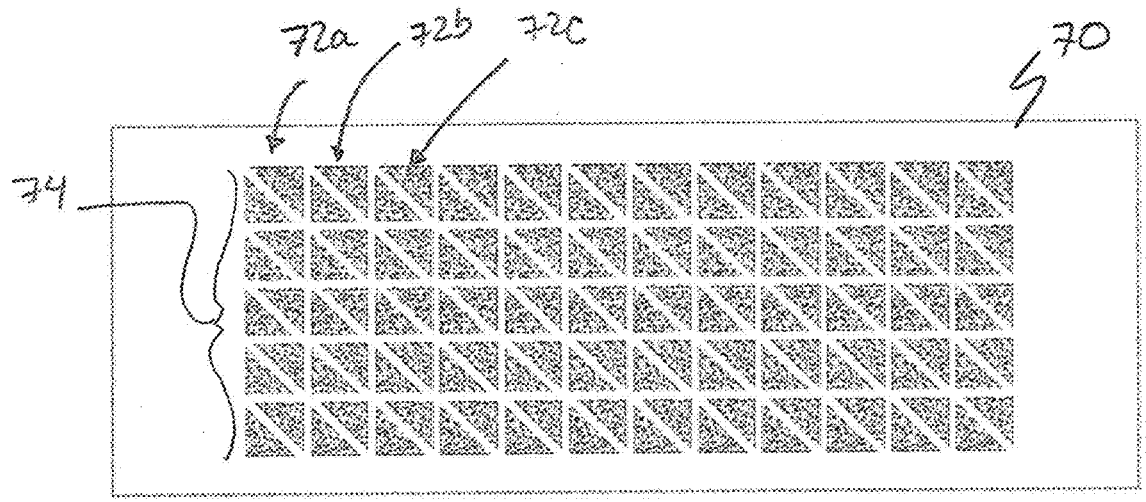
FIG. 7B shows one embodiment of a low frequency transducer element dicing pattern in accordance with an embodiment of the disclosed technology.

In one embodiment, the sheet of PZT is diced into a number of columns of triangular pillars as a 1-3 composite as best shown in FIG. 7B. In the example shown, each column 72a, 72b, 72c of triangular elements 74 is treated as a single transducer element. In FIG. 7B, only 12 columns of transducer elements are shown for purposes of illustration. In one embodiment, the low frequency transducer includes 32 columns of triangular elements. However, the low frequency transducer could include fewer or a greater number of columns as desired. Furthermore, each transducer element in the low frequency transducer may have other shapes such as small squares or rectangular-shaped elements.

Figure 8:
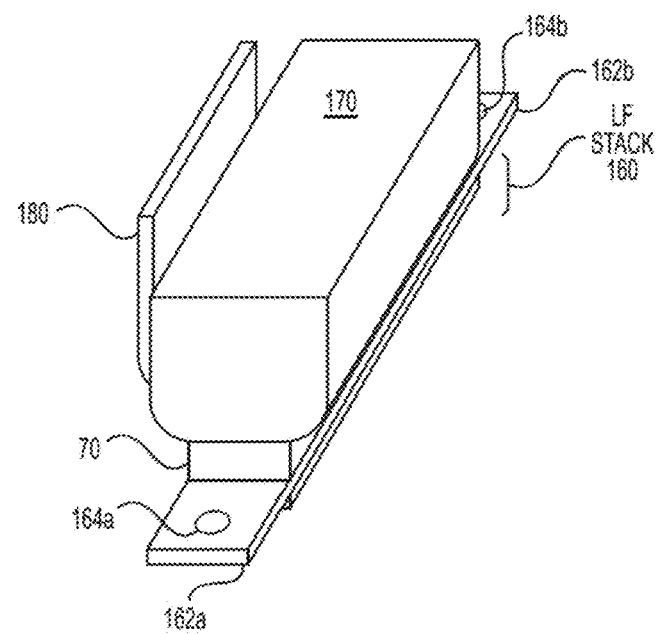
FIG. 8 is an isometric view of a low frequency transducer in accordance with some embodiments of the disclosed technology.

FIG. 8 is an isometric view of a low frequency transducer in accordance with an embodiment of the disclosed technology. The low frequency transducer includes the piezoelectric layer 70, one or more matching layers 160 positioned ahead of (e.g. in front of) the piezoelectric layer 70 and a backing layer 170 positioned behind the transducer elements. A flex circuit 180 includes signal traces that are electrically connected to individual low frequency transducer elements. The low frequency transducer also includes a pair of alignment tabs 162a, 162b. In one embodiment, the alignment tabs are Kapton™ sheets inserted into an epoxy matching layer at a position away from the position of the low frequency transducer elements so as not to interfere with the operation of the low frequency transducer. Other materials for the alignment tabs could also be used such as alumina. Holes 164a, 164b are placed in the alignment tabs at a known distance from the low frequency transducer elements. The holes are placed over a fiducial on the high frequency transducer in order to precisely align the low frequency transducer elements with respect to the high frequency transducer elements.

In one embodiment, the holes 164a, 164b in the alignment tabs 162a, 162b are placed over the fiducials on the intermediate layer. If the alignment tabs are long enough, the holes in the alignment tabs could be placed over the fiducials marked on the support frame in order to align the low frequency transducer with respect to the high frequency transducer.

FIG. 9A is a cross-sectional view of a low frequency transducer in accordance with one embodiment of the disclosed technology. The transducer includes the piezoelectric layer 70 and two matching layers 160 positioned in front of the piezoelectric layer. The matching layers match the impedance of the low frequency piezoelectric elements to the impedance of the intermediate layer to which the low frequency transducer is secured. A backing layer 170 is positioned behind the low frequency transducer elements. As shown in FIG. 9C, the alignment tabs 162a, 162b are part of a matching layer ahead of the low frequency transducer elements. The holes 164a, 164b in the alignment tabs are positioned at a known distance from the low transducer elements as can be seen in FIG. 9B. A flex circuit 180 extends out from under the backing layer where connections are made to the transducer elements.

Figure 10A:
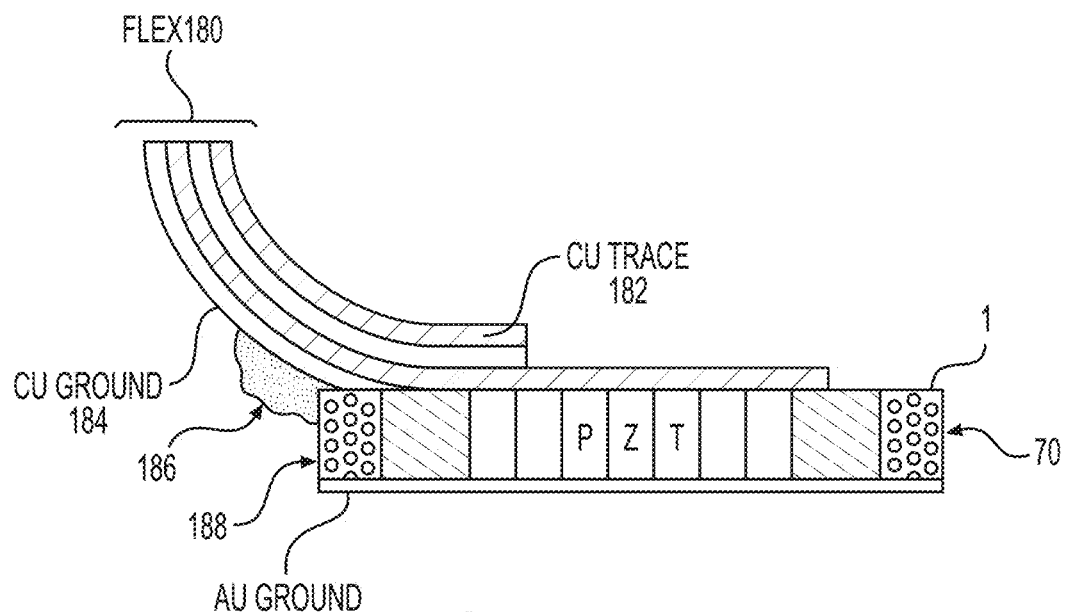
FIGS. 10A and 10B show how connections are made between ground and signal traces in a flex circuit to the electrodes for the low frequency transducer elements and common transducer ground electrode in accordance with one embodiment of the disclosed technology.
Figure 10B:
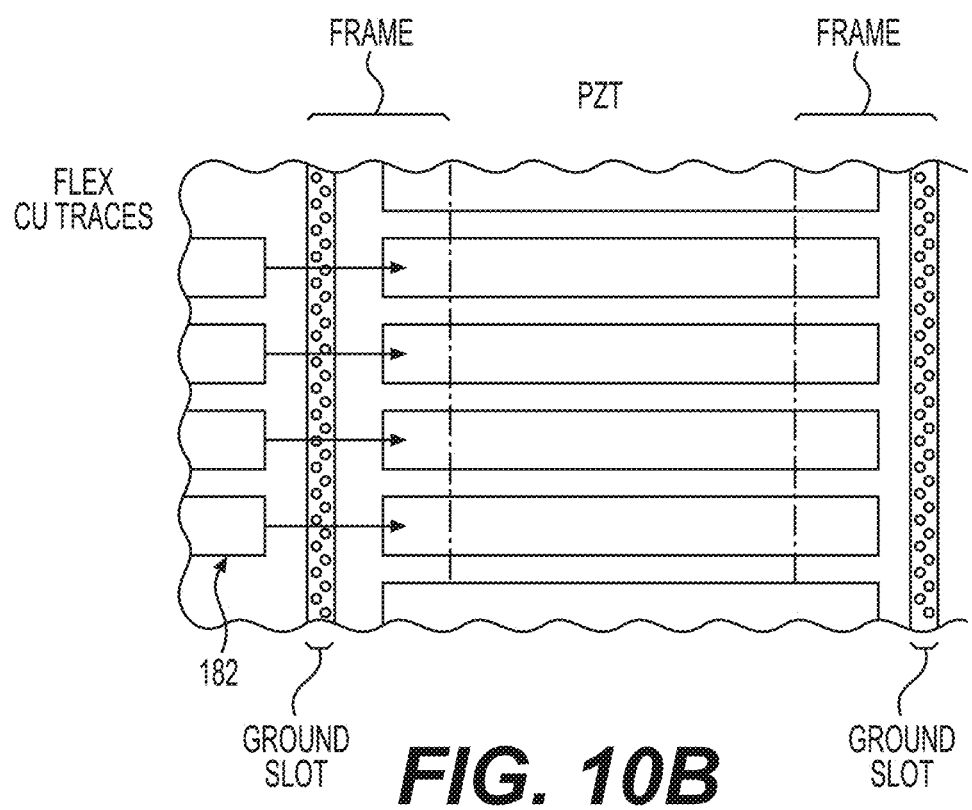

FIGS. 10A and 10B show one way of connecting the signal and ground traces of a flex circuit to the corresponding electrodes in the low frequency array. As shown in FIG. 10A, the flex circuit 180 includes a number of signal traces 182 and a ground trace 184. The ground trace 184 is electrically connected to the ground electrode on the front of the low frequency array with a conductive epoxy 186 joined to conductive epoxy 188 in the notches 80 in the frame 70 or to vias in the frame. As shown in FIG. 10B, the exposed ends of the signal traces 182 can be adhesively secured to the transducer elements with a conductive epoxy. Because the transducer elements of the low frequency transducer are relatively large, they can be easily aligned with the signal traces 182 in the flex circuit 180.

FIG. 11 is a cross sectional view of the dual frequency transducer in accordance with one embodiment of the disclosed technology. The low frequency transducer elements 71 are directly aligned with the high frequency transducer elements 51 by placing the holes on the alignment tabs 162*a*, 162*b* over the fiducials on the intermediate layer. The holes in the alignment tabs are placed at a known location with respect to the low frequency transducer elements and the fiducials are precisely placed at a known location with respect to the high frequency transducer elements. Therefore, placing the holes over the fiducials on the intermediate layer precisely positions the low frequency transducer elements with respect to the high frequency transducer elements without having to align the transducer on a wet bench.

FIG. 12 shows one embodiment of a transducer housing 200 surrounding the dual frequency transducer array. In the embodiment shown the housing includes separate cables 202, 204 connecting the low and high frequency transducers. In one embodiment, the low frequency transducer can be used alone to image tissue with low frequency ultrasound (e.g. in a frequency range of 4-10 MHz). Similarly, the high frequency transducer can be used to image tissue with high frequency ultrasound (e.g. in a frequency range of 20-50 MHz). Alternatively, both transducers can be used to perform imaging such as harmonic or contrast agent imaging where a region of interest is insonified with signals from the low frequency transducer and ultrasound echo signals at harmonics of the excitation frequency are detected with the high frequency transducer.

FIGS. 13A-13H are some sample beam plots of a low frequency transducer operating in a plane wave imaging mode. In one embodiment, a 32-element low frequency transducer is positioned behind a 256 element high frequency transducer. Electrical matching using 1:3 mini-transformers bring the impedance of the low frequency transducer elements from about 500 ohms to about 47.2+/−2.6 ohms with a phase of minus 60.1+/−5.5 degrees. The single low frequency element peak-peak pressures measured at 1.7 mm. from the lens were increased from 0.77 kPa/V without matching to 1.51 kPa/V with matching in the 6-140V range with a variation of about +5% across the elements. In plane wave imaging, pressure is 3 times higher than for a single element. Focusing is observed in the elevation plane at 5.5 mm with a 6 dB beamwidth of 2.7 mm (FIGS. 13A,13C). Past the focus, the pressure drops as the wavefront diverges (FIG. 13E). In the azimuth direction, the beam is relatively uniform (without apodization), with a variation of 2 dB relative to the maximum on the edges (FIGS. 13B,13D). Beam steering is achieved for +/−18 degree angles (FIGS. 13F-13H) allowing for planewave compounding.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A method of manufacturing a dual frequency transducer comprising:
   providing a high frequency (HF) transducer having a first sheet of piezoelectric material including HF transducer elements, one or more matching layers, and a HF frame;
   securing a surface of the first sheet of piezoelectric material to a support frame, the support frame including an epoxy material;
   forming at least one alignment post in the epoxy material;
   marking the at least one alignment post with one or more fiducials;
   positioning, on a first side of the HF transducer elements, an intermediate layer that is configured to absorb HF ultrasound signals, the intermediate layer including at least one slot configured to engage with the at least one alignment post;
   aligning, with the one or more fiducials, a low frequency (LF) transducer including:
      one or more tabs with an alignment feature that aligns the LF transducer with the one or more fiducials;
      a second sheet of piezoelectric material including LF transducer elements; and
      one or more matching layers; and
   securing the one or more matching layers to the intermediate layer.

2. The method of claim 1, wherein the alignment feature comprises a hole on an alignment tab that is at a known position with respect to the LF transducer elements of the LF transducer.

3. The method of claim 1, wherein the intermediate layer is made of silicone powder-doped epoxy.

4. The method of claim 3, wherein a surface of the support frame is filled with an epoxy having a recess into which a portion of the intermediate layer is fitted.

5. The method of claim 4, wherein the intermediate layer is adhered to the recess with the same epoxy in which the recess is formed.

6. The method of claim 1, wherein the intermediate layer is larger than an area of the HF transducer elements in the piezoelectric material of the HF transducer.

7. The method of claim 1, wherein the intermediate layer includes at least one fiducial marked at a known position with respect to the HF transducer elements, and wherein the alignment feature on the LF transducer is aligned with the at least one fiducial on the intermediate layer.

8. The method of claim 1, wherein at least one of the tabs includes a hole to place over the one or more fiducials on the HF transducer.

9. The method of claim 1, wherein the one or more tabs in the LF transducer are incorporated into the one or more matching layers of the LF transducer.

10. The method of claim 1, wherein the first sheet of piezoelectric material further comprises an outer perimeter with an edge, and wherein the support frame surrounds the outer perimeter of the first sheet of piezoelectric material and is spaced from the edge of the outer perimeter such that kerf cuts that define individual transducer elements in the first sheet of piezoelectric material extend across a full width of the first sheet of piezoelectric material.

11. A method of manufacturing a dual frequency transducer comprising:
   providing a high frequency (HF) transducer comprising a sheet of piezoelectric material including a number of HF transducer elements;
   providing a backing material that is constructed to absorb HF ultrasound signals and pass low frequency (LF) ultrasound signals;
   providing one or more fiducials marked on a first side of the HF transducer elements at a known position with respect to the HF transducer elements; and
   providing an LF transducer including a number of LF transducer elements including one or more alignment tabs that are positioned using the one or more fiducials to align the LF transducer elements with the HF transducer elements.

12. The method of claim 11, further comprising incorporating the one or more alignment tabs in the LF transducer into a matching layer of the LF transducer.

13. The method of claim 12, further comprising securing the one or more alignment tabs in an epoxy layer that forms the matching layer.

14. The method of claim 13, further comprising aligning the LF transducer elements with respect to the HF transducer elements by placing a hole in the one or more alignment tabs over the one or more fiducials.

15. A method of manufacturing a dual frequency transducer comprising:
    providing a high frequency (HF) transducer including
        a first sheet of piezoelectric material including a number of HF transducer elements,
        one or more matching layers, and
        a support frame on a back side of the piezoelectric material configured to support one or more flex circuits with first signal traces that connect to the HF transducer elements;
    providing one or more fiducials marked at known positions with respect to the HF transducer elements;
    providing an intermediate layer that is configured to absorb HF ultrasound signals and positioned on a first side of the HF transducer elements; and
    providing a low frequency (LF) transducer including
        a second sheet of piezoelectric material including a number of LF transducer elements,
        one or more matching layers, and
        a flex circuit with second signal traces that connect to the LF transducer elements, wherein the LF transducer includes one or more tabs with an alignment feature that aligns the LF transducer with a fiducial.

16. The method of claim 15, wherein the alignment feature comprises a hole on an alignment tab that is at a known position with respect to the LF transducer elements of the LF transducer.

17. The method of claim 15, wherein the intermediate layer is made of silicone powder-doped epoxy.

18. The method of claim 17, wherein the support frame has a surface and wherein the surface of the support frame is filled with an epoxy having a recess into which a portion of the intermediate layer is fitted.

19. The method of claim 18, wherein the intermediate layer is adhered to the recess with the same epoxy in which the recess is formed.

20. The method of claim 15, wherein the first sheet of piezoelectric material further comprises an outer perimeter with an edge, and wherein the support frame surrounds the outer perimeter of the first sheet of piezoelectric material and is spaced from the edge of the outer perimeter such that kerf cuts that define individual transducer elements in the first sheet of piezoelectric material extend across a full width of the first sheet of piezoelectric material.

\* \* \* \* \*